United States Patent [19]

Batchelor et al.

[11] 4,452,991

[45] Jun. 5, 1984

[54] FLAVAN DERIVATIVES USEFUL FOR IMPAIRING RNA VIRUS REPLICATION IN A CELL

[76] Inventors: John F. Batchelor, 10 Wilton Pl., Beckenham, Kent; Jeremy G. Vinter, 76 South Ter., Dorking, Surrey RH4 2AQ; Harold F. Hodson, 69 Whitecroft Way, Park Langley, Beckenham, Kent, all of England

[21] Appl. No.: 302,109

[22] Filed: Apr. 9, 1981

Related U.S. Application Data

[62] Division of Ser. No. 177,127, Aug. 11, 1980, abandoned.

[30] Foreign Application Priority Data

Sep. 13, 1979 [GB] United Kingdom ............... 7931841

[51] Int. Cl.³ .................. C07D 311/60; C07D 311/78
[52] U.S. Cl. .................................... 549/383; 549/384; 549/406; 424/283
[58] Field of Search ....................... 549/406, 383, 384

[56] References Cited

U.S. PATENT DOCUMENTS

3,433,805  3/1969  Krämer et al. ..................... 549/406
3,462,455  8/1969  Krämer et al. ..................... 549/406

OTHER PUBLICATIONS

Tyrrell et al., J. Antimicrob. Chemo. 9, 340 (1982).
Andrieux et al., Bull. Soc. Chim. France, 1967 (1976).
Descotes et al., Tet. Lett., 39, 3395 (1969).
Batchelor et al., Chem. Abst., 95, 42,910p (1981)—Abstract of Eur. Pat. Appl. 25,599.

*Primary Examiner*—Nicky Chan
*Attorney, Agent, or Firm*—Donald Brown

[57] ABSTRACT

A method of treating or preventing viral infections, in particular rhinovirus infections comprising the administration of an effective amount of a flavan derivative of formula (I).

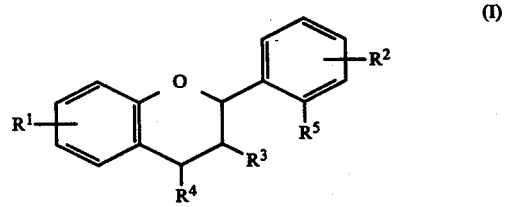

Pharmaceutical compositions containing these compounds, and some novel compounds are also disclosed.

8 Claims, No Drawings

FLAVAN DERIVATIVES USEFUL FOR IMPAIRING RNA VIRUS REPLICATION IN A CELL

This is a division of application Ser. No. 177,127 filed Aug. 11, 1980, now abandoned.

The present invention relates to certain flavan derivatives which are useful as medicaments. In particular such compounds are antiviral agents, and especially suitable for the prevention and treatment of rhinoviral infections. The invention also relates to processes for the production of these compounds, to pharmaceutical formulations containing them and to methods of treatment employing them.

In the majority of instances, the disease known as the "common cold" is caused by rhinoviral infections, although "colds" may also be caused by infection of the upper respiratory tract by .e.g. corona- and enteroviruses and allergic reactions may be mistaken for colds. Mankind throughout the world is prone to rhinoviral infections, which are a major cause of absence from work through illness. The prevention and treatment of such diseases is thus of great economic importance.

Once infected by a rhinovirus, an individual retains immunity to that serotype, which may be enhanced by continual reinfection if the serotype is prevalent in the community. There is however, no cross-immunity between serotypes and thus a cold is usually experienced by an individual whenever a new serotype of rhinovirus is encountered; on average about twice or three times a year.

Immunisation against rhinovirus is not practicable because there are about 120 known serotypes of rhinovirus and a vaccine against all these would overload the vaccinee's system.

It would therefore appear that chemotherapy is the only suitable method for preventing or treating rhinoviral infections. Much research effort has been expended in recent years but no effective chemotherapeutic agent has yet emerged.

It has now been found that certain derivatives of flavan in which the pyran ring bears one or more substituents, are active against rhinovirus, and against other viruses such as coronavirus.

According to the present invention therefore there is provided a compound of formula (I)

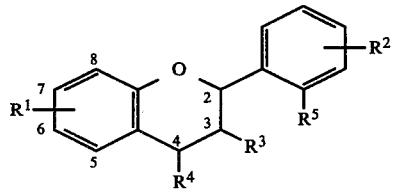
(I)

as a medicament, or a pharmaceutically acceptable formulation thereof wherein $R^4$ is a hydrogen atom or a lower alkyl group and $R^3$ is a hydrogen atom or a lower alkyl group, and $R^5$ is a substituent, or $R^3$ and $R^5$ together form a group —CH$_2$— or —CH$_2$—CH$_2$— and $R^1$ and $R^2$ each represent four substituents or one or both of $R^1$ and $R^2$ represents a methylenedioxy group and two substituents, each of the aforementioned substituents being independently selected from hydrogen and halogen atoms, (lower)alkyl, hydroxy (lower)alkyl, carboxy(lower)alkyl, (lower)alkoxy, amino, (lower)alkylamino, di(lower)alkylamino, acylamino, nitro, cyano, trifluoromethyl, carboxyl and hydroxyl groups: provided that at least one of $R^3$ and $R^4$ is not a hydrogen atom, and salts or esters of such compounds, where appropriate such a compound being particularly suitable for treating or preventing viral, especially rhinoviral diseases.

As used herein the expressions "(lower)alkyl" and "(lower)alkoxyl" and cognate terms, mean branched or straight chain alkyl or alkoxy groups having from 1 to 4 carbon atoms.

As used herein the expression "acylamino" means an amino group substituted with the residue of a carboxylic acid, in particular a (lower)alkyl, aryl(lower)alkyl or aryl carboxylic acid.

Whenever a compound of formula (I) bears a hydroxyl, amino or carboxyl group, salts and esters may be formed, and these are encompassed within the present invention. It is preferred that the salts and esters be pharmaceutically acceptable. A discussion of the properties and desirability of various salts is given in "pharmaceutical salts" by S. M. Berge et al, *J. Pharm. Soc.* 66, 1 (1977).

For the purposes of the present description, a numbering system as shown in formula (I) has been adopted and substituents on the phenyl ring are numbered from 2' to 6' and is used throughout in relation to the general formulae of this specification. However, when $R^3$ and $R^5$ together form —CH$_2$— or —CH$_2$—CH$_2$ groups, this system is at variance with the accepted chemical nomenclature, and in these instances, when specific chemical compounds are named, such as in the Examples below, the correct chemical name is given. Thus a compound wherein $R^3$ and $R^5$ together form a —CH$_2$— group, is named as a derivative of pyran, e.g.

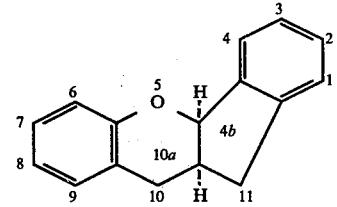

cis-4b, 10, 10a, 11-tetrahydrobenz(b)indeno(2,1-e)pyran and when $R^3$ and $R^5$ together form a —CH$_2$—CH$_2$— group, the compound is named as a derivative of xanthene, e.g.,

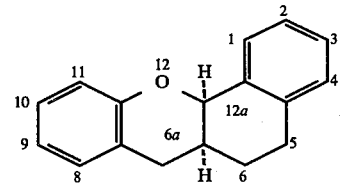

cis-5,6,6a,12a-tetrahydro-7H-benzo(c)xanthene.

It will be noticed that compounds of formula (I) may exist in various stereoisomeric forms depending upon the configuration of the substituents on the carbon atoms designated 3 and/or 4 in formula (I) in relation to the phenyl group on carbon atom 2. Whilst the present invention encompasses all the possible enantiomers, diastereoisomers and geometrical isomers of compounds of formula (I), certain stereoisomers are preferred because they have enhanced antiviral activity. In particular, when $R^3$ is an alkyl group it is preferred that this group be in the trans-configuration with respect to the phenyl group, but when $R^3$ is, together with $R^5$, a —$CH_2$— or —$CH_2$—$CH_2$— group, it is preferred that $R^3$ and the phenyl group are in the cis-configuration.

It is preferred that one of $R^3$ and $R^4$ is a hydrogen atom whenever $R^3$ or $R^4$ is a (lower) alkyl group and it is preferred that the alkyl group has from 1 to 3 carbon atoms.

Whilst $R^1$ and $R^2$ may each represent up to four atoms or groups other than hydrogen atoms, it is preferred that at least two of the substituents represented by $R^1$ and at least two of the substituents represented by $R^2$ are hydrogen atoms. More preferably $R_1$ and $R^2$ each represent at least three hydrogen atoms.

Particularly preferred substituents are hydrogen and halogen atoms, and amino, hydroxyl, methyl, ethyl, methoxy, ethoxy, hydroxymethyl, trifluoromethyl, and cyano groups.

It is preferred that substituents other than hydrogen atoms, represented by R' are located at the 6, and/or 7 positions of a flavan derivative of formula (I) most preferably at the 6 position and that substituents other than hydrogen atoms, represented by $R^2$, are located at the 3', 4' and/or 5' positions most preferably at the 4' position.

Compounds of formula (I) are more preferred as medicaments, or in pharmaceutical formulations when they conform to formula (IA) ferred embodiments of the present invention. The most preferred compounds of formula (I) as medicaments or in pharmaceutical formulations are those of formula (IA) wherein $R^4$ is a hydrogen atom and $R^3$ is a methyl group or a hydrogen atom and $R^5$ is hydrogen atom, or $R^3$ and $R^5$ together form a group —$CH_2$— or —$CH_2$—$CH_2$—, especially the following, namely:

trans-3-methylflavan
trans-4',6-dichloro-3-methylflavan
cis-4b,10,10a,11-tetrahydrobenz(b)indeno(2,1-e)pyran
cis-8-chloro 4b,10,10a11-tetrahydrobenz(b)indeno(2,1-e)pyran
cis-2-chloro 4b,10,10a,11-tetrahydrobenz(b)indeno(2,1-e)pyran
cis-2,8-dichloro 4b,10,10a,11-tetrahydrobenz(b)indeno(2,1-e)pyran
cis-5,6,6a,12a-tetrahydro-7H-benzo(c)xanthene
cis-3-chloro 5,6,6a,12a-tetrahydro-7H-benzo(c)xanthene
cis-9-chloro 5,6,6a,12a-tetrahydro-7H-benzo(c)xanthene.

In second aspect of the present invention there is provided a novel compound of formula (II)

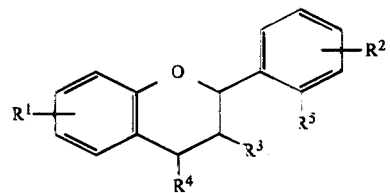

(II)

wherein $R^1$, $R^2$, $R^3$, $R^4$ and $R^5$ are as defined hereinbefore with respect to compounds of formula (I), or a salt or ester thereof where appropriate, except for the following known compounds, namely:

| | |
|---|---|
| trans-3-methylflavan | Tet. letters, 60,5279, (1969) |
| 4'6-dihydroxy-3-methylflavan | C.A., 72, P100520z |
| 4',8-dimethoxy-3-methylflavan | C.A., 66,85221h |
| 4'-hydroxy-6-methoxy-3-methylflavan | Tetrahedron, 23, 057, (1967) |
| 4',6-dimethoxy-3-methylflavan | ibid. |
| 6-hydroxy-4'-methoxy-3-methylflavan | UK Pat. No. 1022745 |
| 6-acetoxy-4'-methoxy-3-methylflavan, | ibid. |
| 6-acetoxy-3',4'-methylenedioxy-3-methylflavan, | ibid. |
| cis-6-hydroxy-3-methylflavan, | UK Pat. No. 1087539 |
| cis-6-acetoxy-3-methylflavan, | ibid. |
| cis-3-propylflavan | ibid. |
| trans-6-hydroxy-3-methylflavan | ibid. |
| trans-6-methoxy-3-methylflavan, | ibid. |
| 4b,10,10a,11-tetrahydrobenz(b)indeno(2,1-e)pyran | Tet. letters, 39, 3395, (1969) and Bull. Soc. Chim. France, 967, (1976) |
| 6, 8-dimethyl-4b,10,10a,11-tetrahydrobenz(b)indeno(2,1-e)pyran | J. Prakt. Chem., 158, 275, (1941) |

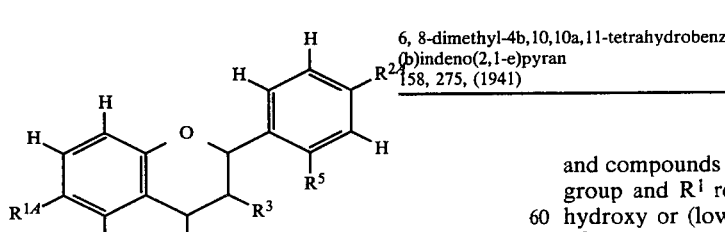

wherein $R^3$, $R^4$ and $R^5$ are as hereinbefore defined and $R^{1A}$ and $R^{2A}$ each represent a single substituent selected from the class defined with respect to $R^1$ and $R^2$.

Compounds of formula (I) and especially of formula (IA) representing a conjunction of two or more of the preferences stated hereinbefore are particularly pre- and compounds wherein $R^3$ is a methyl, ethyl or propyl group and $R^1$ represents three hydrogen atoms and a hydroxy or (lower)alkoxy group at the 6 position and $R^2$ represents three hydrogen atoms and a hydroxyl group at the 4' position or two hydrogen atoms and a methylene dioxy group at the 3', 4'-position (U.K. No. 1022745).

A variety of processes is available for the production of compounds of formulae (I) and (II), these being analogous to methods which are well known and used in the art of flavanoid synthesis, in particular to those described in the literature cited hereunder in relation to processes (a) to (d).

(a) Flavan derivatives are generally prepared by the reduction of a double bond in, or of substituent groups on the pyran ring. Thus flavones, flavanones, flavenes, flavylium salts and 3 or 4-hydroxy, mercapto or halogeno substituted flavans may be reduced by well known methods (Refs 1 to 11, 21). Flavenes may also be converted to flavans by a disproportionation reaction (Ref 12). By forming the dithioketal and then reducing it with Raney nickel, flavanones can be converted to flavans (13).

In addition exocyclic double bonds and other reducable moieties in precursors for $R^3$ and $R^4$ such as alkenyl or alkylidene groups may be reduced to povide a compound of formula (I), as may oxo-substituents on the $R^3$, $R^5$ linkage of the 5,6,6a,12a-tetrahydro-7H-benzo(c)xanthene and 4b,10,10a,11-tetrahydrobenz(b)indeno(2,1-e)pyrans of formula (I).

(b) Alternatively, flavans can be obtained by reduction and cyclisation of 2-hydroxychalcones. Thus substituted 1-phenyl-3-(2-hydroxyphenyl)-propan-1-ols are produced by reduction of a 2-hydroxychalcone using sodium borohydride and converted to flavans by acid catalysed ring closure (Refs 6, 12, 14). Combined reduction and cyclisation of 2-hydroxychalcones is effected using lithium aluminium hydride and aluminium chloride (Ref 8). Catalytic reduction of the 2-hydroxychalcone affords the corresponding dihydrochalcone, from which flavan is obtained by treatment with zinc chloride in benzene (Ref 15), (c) A third technique for producing the flavan ring system is the condensation of 2-hydroxymethylphenol or the quinone methide obtained therefrom with an aromatic olefin derivative, the reaction being effected thermally or in certain cases by acid catalysis, using a proton acid or a Friedel Crafts type catalyst. Thus 2-hydroxymethylphenol condenses to a flavan derivative (Refs. 3,5, 16, 22)

Phenol derivatives can be condensed with, for instance, 2-bromomethyl-1-phenyl prop-1-ene (Ref 5 and 6).

(d) Once the flavan nucleus has been prepared further compounds of formula (I) or (II) may be produced by addition, replacement or elimination or modification of the substituents on the aromatic rings although it is usually more convenient to use starting materials which already bear the requisite substituents. When a substituent, such as a hydroxyl or amino group could inerfere with the desired synthetic process, it may of course be blocked by conventional means and later deblocked to afford the desired flavan derivative.

Flavanones, flavones, flavenes and flavylium salts used as starting materials for the production of flavans may themselves be prepared by known methods. In particular, 2-hydroxychalcones may be cyclised to flavylium salts, whilst 2'-hydroxychalcones can be reduced and then cyclised to the flavenes, or may be cyclised directly, affording flavanones. Chalcones are, in turn produced by the Knoevenagel condensation of appropriately substituted acetophenone and benzaldehyde derivatives. (Ref 19).

Salts and esters of compound of formula (I) may be produced by standard methods, such as metathetical reactions.

Where appropriate, when preparing compounds of formula (I) and (II), particular attention should be payed to the stereochemistry of the reactions employed, since some are more suitable for obtaining cis isomerws and others are better adopted to the production of the trans isomers. Obviously not all the reactions are stereospecific or stereoselective, and in these cases separation steps such as chromatography may be required in order to obtain a particular geometric isomer in a pure form.

By selecting a particular enantiomer of a starting material and using an asymmetric synthesis, an optically pure enantiomer of a compound of formula (I) or (II) may be obtained (e.g. Ref. 20). Alternatively, where suitable, resolution of a compound of formula (I) may be possible by the use of asymmetric reagents or chromatographic media.

Literature cited in relation to processes for producing flavans

1. E. L. Martin, *Organic Reactions,* 1 161, (1942)
2. E. Vedejs, *Organic Reactions,* 22, 412, (1974)
3. B. L. Verma, et al., *Indian J. Chem.,* 3(12), 565, (1965)
4. M. M. Bokadia and B. L. Verma, *Chem. and Ind.,* 235, (1964)
5. British Patent Specification No. 1022745
6. British Patent Specification No. 1087539
7. U.S. Pat. No. 3,555,047
8. M. M. Bokadia, et al., *J. Chem. Soc.,* 1658, (1962)
9. J. W. Clark-Lewis and R. W. Jemison, *Austral. J. Chem.,* 21, 2247, (1968)
10. M. Suzuki, et al., *Nippon Kagaku Zasshi,* 89 (a), 878, (1968) and ibid, 90 (4), 397, (1969).
11. R. Mozingo and H. Adkins, *J. Am. Chem. Soc.,* 60, 669, (1938)
12. L. Jurd, *Tetrahedron,* 23, 1057, (1967)
13. E. J. Keogh, et al., *Chem. and Ind.,* 2100, (1961)
14. L. Jurd, *Chem and Ind.,* 2175, (1967)
15. Van Allan, et al., *J. Org. Chem.,* 32, 1897, (1967)
16. R. R. Schmidt, *Tet.letters,* 60,5279, (1969)
17. K. Hultzch, *J. Prakt. Chem.,* 158, 275, (1941)
18. M. Wakselman and M. Vilkas, *C. R. Hebd. Seance. Acid. Sci.,* 258, 1526 (1964)
19. Nielsen, *Organic Reactions,* 16, 44 (1968)
20. Coney and Mitra, *J. Am. Chem. Soc.,* 84, 2938, (1962)
21. J. Andrieux, et al., *Bull. Soc. Chem. France,* 1967, (1976)
22. G. Descotes and A. Jullien, *Tet. Letters,* 39, 3395, (1969).

While it is possible for the compound of formula (I) or, where appropriate pharmaceutically acceptable salts thereof (hereinafter referred to as the "active compounds") to be administered as the raw chemical it is preferred that the active compound is presented in the form of a pharmaceutical composition.

In a further aspect of the invention therefore provided a pharmaceutical formulation comprising the active compound together with a pharmaceutically acceptable carrier therefor. The carrier must be "acceptable" in the sense of being compatible with the other ingredients of the formulation and not deleterious to the recipient thereof. Such carriers are solid, liquid or gaseous materials recommended for the purpose of administering the medicament.

These pharmaceutical compositions may be administered orally or parenterally (including subcutaneous, intramuscular and intravenous injection) or as a suppository or pessary or may be applied topically or as an ophthalmic solution or may be inhaled. It is preferred that the compositions are administered orally or inhaled. The terms formulation and composition are used synonomously.

For oral administration the pharmaceutical compositions may be presented as a draugt in water or in a syrup, in capsules, cachets, boluses or tablets, as an aqueous or oleaginous solution or suspension or in suspension in a syrup, such suspensions optionally including suspending agents or as an oil-in-water or water-in-oil emulsion. Where desirable or necessary flavouring, sweetening, preserving, thickening or emulsifying agents may be included in the formulation.

Tablets may contain the active compound as a powder or granules optionally mixed with binders, lubricants, inert diluents or surface-active or dispersing agents and may be formed by compression or by moulding in inert liquid diluent. Such tablets may be optionally scored and/or coated.

Capsules and cachets may contain the active compound alone or in admixture with one or more accessary ingredients. Capsules may also contain the active compound in aqueous or oleaginous solution suspension or emulsion optionally in association with accessory ingredients.

For administration as a suppository or pessary the active compound may be presented in admixture with a suitable carrier such as cocoa butter and other material commonly used in the art, the formulation conveniently being shaped by moulding.

For administration in discrete dosage forms such as the tablets, capsules, suppositories and pessaries described above, the active compound is preferably presented at 10 µg to 10 mg, most preferably 0.1 mg to 10 mg per tablet, capsule, suppository or pessary.

For parenteral administration the active compound may be presented in sterile solutions or suspensions in aqueous or oleaginous vehicles, which may also contain preservatives and material for rendering the solution or suspension isotonic with the blood of the intended recipient. Such formulations may conveniently be presented in unit-dose or multi-dose sealed containers.

For topical administration the composition may be presented in ointments creams, lotions, pastes, jellies, sprays, aerosols and bath oils. Ointments and creams may contain oleaginous absorption colloidal clays, thickening agents such as gum tragacanth or sodium alginate and other pharmaceutically acceptable accessory ingredients such as humectants, preservatives, buffers and antioxidants which are useful in such formulations.

For administration as eye drops, active compound is presented in sterile water with excipients such as antimicrobial agents and antioxidants as a relatively dilute solution.

For administration orally in liquid form or parenterally or as eye drops, the active compounds are preferably presented in solution or suspension or emulsion at a concentration of from 0.1 to 10%, more preferably 0.2 to 5% w/v in unit multi-dose form. When presented in unit dose form, it is preferred that each dose-unit contains 0.1 mg to 100 mg, preferably 1 mg to 10mg of active compound.

For inhalation the active compound may be presented in association with volatile excipients as a cream, lotion, paste or ointment or as a finely divided dry powder or in solution for inhalation through a nasal spray, atomiser or insufflator.

All the above formulations are produced by processes which comprise bringing into association the active compound and one or more carriers.

According to the present invention there is therefore provided a process for producing a pharmaceutical formulation of a compound of formula (I) comprising bringing into association a compound of formula (I) and a pharmaceutically acceptable carrier therefore.

Compounds of formula (I) may be administered to human beings and to other animals to treat or prevent viral diseases, especially rhinoviral infections. The dosage administered obviously depends on the activity of the compound and also on the speed with which it is absorbed into the body and on other well-known pharmaceutical considerations, however it is recommended that the active compound is administered at from 2 µg to 10 mg/kg of animal body weight per day, preferably from 25 µg to 1 mg/kg/day and most preferably about 0.1 mg to 0.3 mg/kg/day. The active compound may be administered once or several times daily.

In a further aspect of the present invention there is therefore provided a method for treating rhinoviral infections comprising the administration in an effective dose of a compound of formula (I) or a pharmaceutical formulation than to a human being or other animal.

In a yet further aspect of the present invention there is provided a method for preventing rhinoviral infection comprising the administration in an effective dosage of a compound of formula (I) of a pharmaceutical formulation thereof, to an apparently healthy human being or other animal.

As used herein the term "effective dosage" means that quantity of a compound of formula (I) which is sufficient to cure or prevent a rhinoviral infection.

The invention will now be illustrated with reference to the following Examples, which are not intended to limit the invention in any way.

Temperatures are given hereunder in degrees Celsius. Pressures are given hereunder in millimeters of mercury ("mmHg"). 1mmHg=133.322 Pa.

EXAMPLE 1

Preparation of trans-3-methylflavan (a) o-Hydroxypropiophenone (25.0 g.) and benzaldehyde (17.67 g.) were dissolved in ethanol (200 ml) and stirred while a solution of potassium hydroxide pellets (35.0 g) in water (50 ml) was added. The resulting solution was boiled under reflux for 2 hr, cooled, and acidified with hydrochloric acid. The product was extracted into dichloromethane, washed with water, and the organic solution dried and distilled in vacuo to give a first fraction of o-hydroxypropiophenone (16.2 g, b.pt. 60°/0.25 mmHg.) and a main fraction of 2'-hydroxy-α-methylchalcone (20.1 g., b.pt. 144°–154°/0.5 mmHg).

(b) 2'-Hydroxy-α-methylchalcone (10.0 g) was boiled under reflux with a solution of phosphoric acid (85%, 20 ml) in 2-methoxyethanol (120 ml) for 5 hr. The cooled solution was diluted with water and extracted with dichloromethane. The dried organic layer was distilled using short-path apparatus to give a crystallisable oil, b.pt. 135°–155°/0.5 mm. Recrystallisation from ethanol gave trans-3-methylflavanone (3.9 g. m.pt. 99°–100°).

(c) Trans-3-methylflavanone (3.50 g.) was dissolved in acetic acid (120 ml) and concentrated hydrochloric acid (15 ml) and the solution added to amalgamated zinc prepared from zinc powder (25.0 g) and mercuric chloride (1.0 g). The mixture was stirred for 1 hr. at room temperature, then allowed to stand at room temperature for a further 16 hr. The zinc residue was filtered off, washing with acetic acid, and the filtrate and washings diluted with water and extracted with toluene. The extract was washed with saturated sodium bicarbonate solution, dried, and evaporated. The residue was recrystallised from methanol three times to yield the required trans-3-methylflavan (1.00 g., m.pt. 77°–78°). The configuration was confirmed by $^1$H n.m.r.

Microanalysis: Theory: C: 85.71%, H: 7.19%, Found: C: 85.74%, H: 7.09%.

EXAMPLE 2

Preparation of trans-4',6-dichloro-3-methylflavan

The title compound was prepared by a method exactly analogous to that used in Example I:

(a) 4,5'-Dichloro-2'-hydroxy-α-methylchalone; yellow needles from ethanol, m.pt. 100°–102°
(b) Trans-4',8,6-dichloro-3-methylflavanone; crystals from 80°–100° petroleum ether, m.pt. 123°–125°.
(c) Trans-4',6-dichloro-3-methylflavan; colourless needles from ethanol, The configuration was confirmed by $^1$H.n.m.r. m.pt. 135°–137°.

Microanalysis: Theory: C: 65.55%, H: 4.81%, Found: C: 65.70%, H: 4.69%.

EXAMPLE 3

Preparation of cis-3-methylflavan (a) 2-Hydroxy-α-methylchalone (20.1 g) was dissolved in ethanol (200 ml) and stirred while sodium borohydride (6.39 g) was added in small portions. After 3 hr. stirring at room temperature the mixture was acidified by addition of acetic acid (9.0 ml.) and the precipitated intermediate was extracted into dichloromethane. The extract was washed with saturated brine, dried and evaporated. The residue was heated on a steam bath with acetic acid (100 ml) for 2 hr. The acetic acid was evaporated and the residue chromatographed on alumina, eluting with toluene. The oil thus obtained yielded pure 3-methyl-2H-flav-3-ene on trituration with 40°–60° petroleum ether as colourless crystals (5.0 g., m.pt. 79°–80°).

(b) 3-Methyl-2H-flav-3-ene (5.0 g.) was dissolved in acetic acid (100 ml) and hydrogenated at room temperature and atmospheric pressure using 10% palladium on carbon catalyst (200 mg). When hydrogen uptake was completed the solution was filtered and evaporated, and the residue chromatographed on neutral alumina, eluting with toluene/60°–80° petroleum ether (1:1). Two equal fractions (1.15 g each) were obtained, the faster running fraction comprising entirely the cis-3-methylflavan, and the slower a small proportion of the trans isomer (as observed from the n.m.r. spectrum). The more pure material was distilled in vacuo to yield cis-3-methylflavan, (0.90 g. b.pt. 94°–95°/0.05 mmHg.)

Microanalysis: Theory: C: 85.68%, 7.19%, Found: C: 85.35%, H: 6.92%.

EXAMPLE 4

Preparation of cis-4',6-dichloro-3-methylflaven

The title compound was prepared by a method exactly analogous to that used in Example 3:

(a) 4',6-Dichloro-3-methyl-2H-flav-3-ene. Colourless needles from acetic acid, m.pt. 128°–131°.

(b) Cis-4',6-dichloro-3-methylflavan. Colourless crystals from 60°–80° petroleum ether, m.pt. 79°–80°.

Microanalysis: Theory: C: 65.55% H: 4.81%, Found: C: 65.96%, H: 4.84%.

EXAMPLE 5

Preparation of cis-4b,10,10a,11-tetrahydrobenz(b)indeno(2,1-e)pyran

2-Hydroxybenzyl alcohol (15.0 g) and indene (75 g.) were heated at 210° for 1.5 hr. The unchanged indene was distilled off under reduced pressure and the residue chromatographed on silica gel, eluting with toluene. The product thus obtained, was recrystallised from cyclohexane to yield cis-4b,10,10a,11-tetrahydrobenz(b)indeno(2,1-e)pyran, 2.54 g., m.pt. 59°–60°. The product was characterised by its $^1$H-n.m.r spectrum. Isomeric purity was established by $^{13}$C-n.m.r spectroscopy Microanalysis: Theory: C: 86.44%, H: 6.35%, Found: C: 86.93%, H: 6.15%.

EXAMPLE 6

Preparation of cis-5,6,6a,12a-tetrahydro-7H-benzo(c)xanthene

2-Hydroxybenzyl alcohol (5.0 g) and 1,2-dihydronaphthalene (5.2 g.) were heated together at 190° for 2 hr. the reaction mixture was chromatographed on neutral alumina, eluting with toluene/60°–80° petroleum ether 1:1 to give a solid product which was recrystallised from ethanol to yield colourless crystals of cis-5,6,6a,12a-tetrahydro-7H-benzo(c)xanthene(0.65 g., m.pt. 71°–72°)identified and characterised by $^1$H- and 13C n.m.r. spectra.

Microanalysis: Theory: C: 86.4%, H: 6.83%, Found: C: 86.16%, H: 6.60%.

EXAMPLE 7

Preparation of cis-9,11-dichloro-5,6,6a,12a-tetrahydro-7H-benzo(c)xanthene

The title compound was prepared by a method exactly analogous to that used in Example 6. Cis-9,11-dichloro-5,6,6a,12a-tetrahydro-7H-benzo(c)xanthene was recrystallised from ethanol as colourless crystals, m.pt. 141°–144°.

EXAMPLE 8

Preparation of cis-6-chloro-4b,10,10a,11-tetrahydrobenz(b)indeno(2,1-e)pyran

3-Chloro-2-hydroxybenzyl alcohol (20.0 g) (prepared by the method of Zincke, Hanus and Ziegler, J.Prakt. Chem., (2), 152 126(1939)), and indene (15 ml) were heated together at 190°–200° for 2.5 hr. The crude product was chromatographed on silica gel, eluting with toluene/60°–80° petroleum ether to yield a colourless oil (2.34 g) which was distilled in vacuo to give an oil which crystallised on standing (1.70 g., b.pt. 115°–120°/0.05 mmHg m.pt. 60°–63°). The recrystallised product, from ethanol was identified, by $^1$H-n.m.r., as cis-6-chloro-4b,10,10a,11-tetrahydrobenz(b)indeno(2,1-e) pyran, (1.20 g., m.pt-63°–65°).

Microanalysis: Theory: C: 74.85%, H: 5.11%, Found: C: 74.71%, H: 4.93%.

EXAMPLE 9 TO 12

The compounds of Examples 9 to 12 were prepared by method exactly analogous to that used in Example 8 and purified as described hereunder.

EXAMPLE 9

Cis-6,8-dichloro-4b,10,10a,11-tetrahydrobenz(b)indeno(2,1-e)pyran was recrystallised from ethanol, m.pt. 75°-76°.

Microanalysis: Theory: C: 66.00%, H: 4.16%, Found: C: 65.74%, H: 3.99%.

EXAMPLE 10

Cis-6-hydroxymethyl-8-methyl-4b,10,10a,11-tetrahydroindeno(2,1-e)pyran was chromatographed on silica gel, eluting with chloroform and then distilled in vacuo (b.pt. 155°-160°/0.1 mm). The structure was confirmed by $^1H$ and $^{13}C$ n.m.r. spectroscopy.

Microanalysis: Theory: C: 81.17%, H: 6.81%, Found: C: 81.13%, H: 6.92%.

EXAMPLE 11

Cis-8-chloro-6-hydroxymethyl-4b,10,10a,11-tetrahydrobenz(b)indeno(2,1-e)pyran was chromatographed on silica gel eluting with chloroform and recrystallised from 80°-100° petroleum ether, m.pt. 102°-104°. The structure was confirmed by 1H n.m.r. spectroscopy.

Microanalysis:Theory: C: 71.20%, H: 5.28%, Found: C: 71.06%, H: 5.19%.

EXAMPLE 12

Cis-10-methyl-4b,10,10a,11-tetrahydrobenz(b) indeno(2,1-e)pyran was chromatographed on alumina, eluting with toluene and recrystallised from ethanol, m.pt. 59°-60°.

Microanalysis: Theory: C: 86.4%, H: 6.83%, Found: C:86.17%, H: 6.62%.

EXAMPLE 13 TO 15

By a method exactly analogous to that used in Example 5, the following compounds may be produced and identified by n.m.r. spectroscopy:

| EXAMPLE | COMPOUND |
|---|---|
| 13 | cis-2-chloro-4b,10,10a,11-tetrahydrobenz(b)indeno(2,1-e)pyran |
| 14 | cis-8-chloro-4b,10,10a,11-tetrahydrobenz(b)indeno(2,1-e)pyran |
| 15 | cis-2,8-dichloro-4b,10,10a,11-tetrahydrobenz(b)indeno(2,1-e)pyran |

EXAMPLE 16 TO 18

By a method exactly analogous to that used in Example 6, the following compounds may be prepared and identified by n.m.r. spectroscopy:

| EXAMPLE | COMPOUND |
|---|---|
| 16 | cis-3-chloro-5,6,6a,12a-tetrahydro-7H—benzo(c)xanthene |
| 17 | cis-9-chloro-5,6,6a,12a-tetrahydro-7H—benzo(c)xanthene |
| 18 | cis-3,9-dichloro-5,6,6a,12a-tetrahydro-7H—benzo(c)xanthene |

EXAMPLE 19

Preparation of 4-Methylflavan 1-(2-Hydroxyphenyl)ethanol (33.3 g) and (25.0 g) were heated together at 170° for 2 hr. The reaction mixture was cooled and extracted into ether, and the ether solution washed with 2 M sodium hydroxide solution (3×100 ml), dried, and evaporated. The residue was chromatographed on alumina, eluting with toluene, to yield a colourless oil (3.65 g) which was distilled to give 4-methylflavan (2.80 g), the main cut of 1.64 g. b.pt.135°-15°/0.05 mmHg. High resolution $^1H$ n.m.r. spectroscopy indicated the product to contain a mixture of approximately 88% cis-isomer and 12% trans-isomer.

Microanalysis: Theory: C: 85.68%, H: 7.19%, Found: C: 85.60%, H: 7.37%.

EXAMPLES 20 TO 32

The compounds of Examples 20 to 32 have been prepared by various methods described in the chemical literature mentioned above in relation to processes for producing flavans which methods are specifically incorporated herein by reference to that literature.

(a) 3-Methylflavans

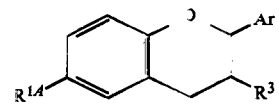

| Example | Ar | $R^3$ | $R^{1A}$ | Ref. |
|---|---|---|---|---|
| 20 | Ph | trans-Me | H | 6 |
| 21 | p-C$_6$H$_4$OH | Me | OMe | 2 |
| 22 | p-C$_6$H$_4$OMe | Me | OMe | 2 |
| 23 | p-C$_6$H$_4$OMe | Me | OH | 5 |
| 24 | p-C$_6$H$_4$OMe | Me | OAc | 5 |
| 25 | (methylenedioxyphenyl) | Me | OAc | 5 |
| 26 | Ph | cis-Me | OH | 5 |
| 27 | Ph | cis-Me | OAc | 5 |
| 28 | Ph | cis-Pr | H | 5 |
| 29 | Ph | trans-Me | OH | 5 |
| 30 | Ph | trans-Me | OMe | 5 |

(b) 4b,10,10a,11-tetrahydrobenz(b)indeno(2,1-e)pyrans

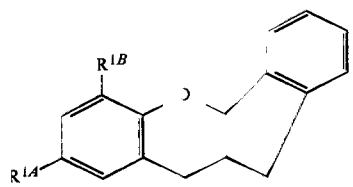

| Example No | $R^{1A}$ | $R^{1B}$ | Ref. |
|---|---|---|---|
| 31 | H | H | 21,11 |
| 32 | Me | Me | 17. |

EXAMPLE 34

Assay of activity of compounds of formula (I)

Activity may be detected by the plaque inhibition (PI) test and measured by the plaque reduction (PR) test. Both assays involve the formation of a monolayer cell culture in a petri dish followed by infection with a virus suspension, and then overlaying the culture with nutrient agarose in the form of a gel. This gel ensures that there is no spread of virus throughout the culture and thus areas of localised cell destruction of plaques are formed.

In the plaque inhibition test a filter paper disc which holds 0.01 ml when impregnated with a solution of compound is placed on top of the agarose gel. The compound may then diffuse throughout the gel so that its greatest concentration will be around the disc and its lowest concentration towards the periphery of the petri dish. The efficacy of the compound may be detected by observing the zone inhibition of plaque formation.

Detectable activity is measured with the plaque reduction assay. A range of concentrations of compound of known molarity are incorporated in the nutrient agarose overlay. Plaque suppression is proportional to compound concentration. Plaque numbers are expressed as percentages of a control, and a dose response curve may be drawn. From this curve 50% of the effective dose ($ED_{50}$) may be estimated.

RESULTS:

| Compound of Example No. | PR ($ED_{50}/\mu M$) |
|---|---|
| 1 | 0.125 |
| 2 | 0.135 (0.029) |
| 3 | 1.1 |
| 5 | 0.38 |
| 6 | 0.03 |
| 7 | 6 |
| 8 | 1.5 (1.7) |
| 9 | 0.57 |

EXAMPLES 35 TO 39

The following compositions were prepared according to the techniques known in the art of pharmacy.

EXAMPLE 35

An inhalant for use in an insufflator was prepared from the following ingredients.

| | |
|---|---|
| trans-3-methylflavan | 0.6 g |
| isopropylmyristate | 10. g |
| Tween 80 | 0.5 g |
| Span 80 | 0.5 g |
| methyl-p-hydroxy-benzoate | 0.1 g |
| Water | to 100 ml |

EXAMPLE 36

A suspension for use as nose drops was prepared from the following ingredients:

| | |
|---|---|
| trans-3-methylflavan | 0.6 g |
| Keltrol | 0.1 g |
| Sodium chloride | 0.5 g |
| sodium lauryl sulphate | 0.1 g |
| Methyl-p-hydroxy-benzoate | 0.1 g |

| | |
|---|---|
| Water | to 100 ml. |

| Capsule 1 | |
|---|---|
| trans-3-methylflavan | 6 g |
| Spray-dried lactose | 300 g |

Gelatin capsules (size 0) were each filled with 500 mg. of the formulation, affording 10 mg. of active ingredient per capsule.

| Capsule 2 | |
|---|---|
| trans-3-methylflavan | 6 g |
| Spray-dried lactose | 208 g |
| Maize starch | 20.8 g |
| Polyvinylpyrollidine | 5.2 g |

Gelatin capsules (size 1) were each filled with 400 mg. of the formulation, affording 10 mg. of the active ingredient per capsule.

EXAMPLE 39

Tablet of trans-3-methylflavan

A tablet formulation containing a mixture of trans-3-methylflavan (10 mg), lactose (90 mg), maize starch (10 mg) and magnesium stearate (1 mg) is prepared by wet granulation.

EXAMPLES 40 TO 53

Tablet formulations, each containing one of the flavan derivatives of Examples 2 to 19 are prepared by a method exactly analogous to EXAMPLE 39.

EXAMPLE 54

Oil formulation of trans-3-methylflavan

| | |
|---|---|
| trans-3-methylflavan | 1 g |
| olive oil B.P. | 1 g |

The compound was dissolved in olive oil for use by oral administration.

EXAMPLES 55 TO 68

Oil formulation of the compounds of Examples 2 to 19 were prepared by a method exactly analogous to that of Example 54.

EXAMPLE 69

Intranasal Administration-Simulation in vitro

Petri dishes were prepared, as for the plaque inhibition test and the confluent sheet of cells was covered with a layer of agarose gel. The compound, trans-3-methylflavan (1 μg) was dissolved in ethanol, and applied to the lids of the petri dishes. When the ethanol had evaporated, leaving the compound spread over the inside of the lids, these were replaced on the petri dishes. Sufficent compound penetrated the agarose layer to cause total inhibition of plaque formation.

We claim:

1. A compound of formula (IA)

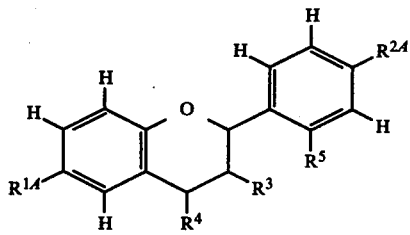

(IA)

wherein $R^4$ is a hydrogen atom or a lower alkyl group and $R^3$ is a hydrogen atom or a lower alkyl group and $R^5$ is hydrogen or $R^3$ and $R^5$ together form a group —$CH_2$— or —$CH_2$—$CH_2$— and $R^{14}$ and $R^{24}$ are the same or different and are selected from halogen atom, cyano, and trifluoromethyl groups; provided that at least one of $R^3$ and $R^4$ is other than hydrogen.

2. The compound of claim 1 which is trans-4', 6-dichloro-3-methylflavan.

3. The compound of claim 1 which is cis-3-chloro 5,6,6a,12a-tetrahydro-7H-benzo(c)xanthene.

4. The compound of claim 1 which is cis-2-chloro 4b,10,10a,11-tetrahydrobenz(b)inden(2,1-e)pyran.

5. The compound of claim 1 which is cis-2,8-dichloro 4b,10,10a,11-tetrahydrobenz(b)indeno(2,1-e) pyran.

6. The compound of claim 1 which is cis-8-chloro 4b,10,10a,11-tetrahydrobenz(b) indeno(2,1-e)pyran.

7. cis-5,6,6a, 12a-tetrahydro-7H-benzo(c)xanthene.

8. The compound of claim 1 which is cis-9-chloro 5,6,6a,12a-tetrahydro-7H-benzo(c)xanthene.

* * * * *